United States Patent
Ziv-Ari et al.

(10) Patent No.: US 11,147,497 B2
(45) Date of Patent: Oct. 19, 2021

(54) MAPPING LOCAL ACTIVATION TIMES FOR SINUS AND NON-SINUS CARDIAC CYCLES

(71) Applicant: BIOSENSE WEBSTER (ISRAEL) LTD., Yokneam (IL)

(72) Inventors: Morris Ziv-Ari, Atlit (IL); Yoav Benaroya, Kfar Saba (IL); Dan Sztejnberg, Hertzliya (IL); Itai Doron, Katsir (IL); Ido Ilan, Yoqneam (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 232 days.

(21) Appl. No.: 16/699,068

(22) Filed: Nov. 28, 2019

(65) Prior Publication Data

US 2021/0161426 A1    Jun. 3, 2021

(51) Int. Cl.
| | |
|---|---|
| A61B 5/343 | (2021.01) |
| A61B 5/364 | (2021.01) |
| A61B 5/339 | (2021.01) |
| A61B 5/06 | (2006.01) |
| A61B 5/35 | (2021.01) |
| A61B 5/361 | (2021.01) |
| A61B 5/363 | (2021.01) |

(Continued)

(52) U.S. Cl.
CPC ............. *A61B 5/343* (2021.01); *A61B 5/066* (2013.01); *A61B 5/339* (2021.01); *A61B 5/35* (2021.01); *A61B 5/361* (2021.01); *A61B 5/363* (2021.01); *A61B 5/364* (2021.01); *A61B 5/367* (2021.01); *A61B 5/743* (2013.01); *A61B 5/287* (2021.01)

(58) Field of Classification Search
None
See application file for complete search history.

(56) References Cited

U.S. PATENT DOCUMENTS

| | | |
|---|---|---|
| 4,336,810 A | 6/1982 | Anderson |
| 5,271,411 A | 12/1993 | Ripley |

(Continued)

FOREIGN PATENT DOCUMENTS

| | | |
|---|---|---|
| EP | 1510172 | 3/2005 |
| WO | WO2000045700 A1 | 8/2000 |

OTHER PUBLICATIONS

European Search Report for corresponding EPA No. 20210154.9 dated Apr. 20, 2021.

*Primary Examiner* — Kennedy Schaetzle (57) ABSTRACT

A method, including receiving sets of signals during multiple cardiac cycles, each set indicating, for a probe inserted into a cardiac chamber, a 3D location of a distal end of the probe, electrical potentials measured at the location, and respective times during a given cycle when the potentials were measured. The received measurements and the respective times are compared to a first template for a sinus rhythm cycle and a second template for a non-sinus rhythm cycle so as to identify a sequence of cycles including consecutive first, second, and third cycles wherein the first and second cycles match the first template and the third cycle matches the second template. A physical map is generated based on the locations. Based on the received locations and corresponding potentials, an electroanatomic map including the local activation times for the non-sinus rhythm cycle overlaid on the physical map is rendered to a display.

21 Claims, 6 Drawing Sheets

(51) Int. Cl.
  *A61B 5/367*  (2021.01)
  *A61B 5/00*  (2006.01)
  *A61B 5/287*  (2021.01)

(56) References Cited

U.S. PATENT DOCUMENTS

| | | | |
|---|---|---|---|
| 6,400,981 B1* | 6/2002 | Govari | A61B 5/06 |
| | | | 600/509 |
| 10,111,598 B2* | 10/2018 | Chauhan | A61B 5/7264 |
| 2009/0099468 A1 | 4/2009 | Thiagalingam | |
| 2009/0275849 A1* | 11/2009 | Stewart | A61B 5/02405 |
| | | | 600/518 |
| 2011/0251505 A1 | 10/2011 | Narayan | |
| 2012/0165895 A1 | 6/2012 | Dong | |
| 2015/0073246 A1 | 3/2015 | Chmiel | |
| 2016/0089048 A1* | 3/2016 | Brodnick | A61B 5/316 |
| | | | 600/512 |
| 2016/0183824 A1* | 6/2016 | Severino | A61B 5/7246 |
| | | | 600/523 |
| 2018/0199847 A1 | 7/2018 | Markovitz | |

* cited by examiner

MAPPING LOCAL ACTIVATION TIMES FOR SINUS AND NON-SINUS CARDIAC CYCLES

FIELD OF THE INVENTION

The present invention relates generally to cardiac mapping, and specifically to mapping local activation times of sinus rhythm and non-sinus rhythm cardiac cycles.

BACKGROUND OF THE INVENTION

Cardiac arrhythmia, such as atrial fibrillation, is a heart rhythm that produces irregular heartbeats. Arrhythmias typically occur when regions of cardiac tissue abnormally conduct electric signals to adjacent tissue, thereby disrupting the normal cardiac cycle and causing asynchronous rhythm.

Mapping of electrical potentials in the heart is a commonly used tool for diagnosing and treating cardiac arrhythmias. Typically, time-varying electrical potentials in the endocardium are sensed and recorded as a function of position inside the heart, and then used to map a local electrogram or local activation time. Activation time differs from point to point in the endocardium due to the time required for conduction of electrical impulses through the heart muscle. The direction of this electrical conduction at any point in the heart is conventionally represented by an activation vector, which is normal to an isoelectric activation front, both of which may be derived from a map of activation time. The rate of propagation of the activation front through any point in the endocardium may be represented as a velocity vector.

Mapping the activation front and conduction fields aids the physician in identifying and diagnosing abnormalities, such as ventricular and atrial tachycardia and ventricular and atrial fibrillation, which result from areas of impaired electrical propagation in the heart tissue.

U.S. Patent Application 2015/0073246 to Chmiel et al., describes a method for manually mapping premature ventricular contractions (PVCs). The method includes recording a series of electrocardiogram (ECG) signals from a patient suffering from PVCs, and then selecting, by a physician, beats which show a sinus rhythm, and beats which show a PVC. The sinus beats are used for producing a physical map of the heart. Electrophysiological readings of local activation times (LATs), acquired during the PVC beats, are then overlaid on the sinus map, producing a so-called LAT hybrid map.

U.S. Pat. No. 5,271,411 to Ripley et al., describes a method for ECG signal analysis and cardiac arrhythmia detection. The method includes identifying a normal QRS complex and labeling QRS complexes acquired after identification the normal QRS complex based on multiple rules and their respective locations.

U.S. Pat. No. 4,336,810 to Anderson et al., describes a method for arrhythmia analysis of ECG recordings. The method includes receiving and comparing ECG signals to known templates that are based on classifications of previously-identified complexes. Based on the comparisons, each of the received signals can be designated as normal, ventricular ectopic, supraventricular ectopic, or unknown (ectopy of unknown origin).

U.S. Patent Application 2012/0165895 to Dong et al., describes a method for non-captured intrinsic discrimination in cardiac pacing response classification. The method includes discriminating non-captured intrinsic beats during evoked response detection and classification by comparing the features of a post-pace cardiac signal with expected features associated with a non-captured response with intrinsic activation. In some embodiments, the detection of a non-captured response with intrinsic activation may be based on the peak amplitude and timing of the cardiac signal.

U.S. Patent Application 2009/0099468 to Thiagalingam et al., describes a method for the automated processing of electrophysiological data. The method includes determining temporal locations by defining one or more reference channels containing a reference beat and comparing beats of the recorded electrogram data against the defined one or more reference channels. An index of the temporal locations and other information of the beats within the recorded electrogram data is created, and the index of temporal locations can be used to analyze recorded electrogram data in order to locate electrophysiological features suggestive of an abnormality.

SUMMARY OF THE INVENTION

There is provided, in accordance with an embodiment of the present invention, a method including receiving, by a processor, sets of signals during multiple cardiac cycles, each set of the signals indicating, for a medical probe inserted into a cardiac chamber, a three-dimensional (3D) location of a distal end of the probe, electrical potentials measured at the 3D location, and respective times during a given cardiac cycle when the electrical potentials were measured. comparing the received electrical potential measurements and the respective times to a first template for a sinus rhythm cardiac cycle and a second template for a non-sinus rhythm cardiac cycle so as to identify a sequence of cardiac cycles including consecutive first, second, and third cardiac cycles wherein the first and second cardiac cycles are in accordance with the first template and the third cardiac cycle is in accordance with the second template, generating a physical map of the cardiac chamber, based on the 3D locations, and rendering to a display, based on the received 3D locations and corresponding measured electrical potentials, an electroanatomic map including the local activation times for the non-sinus rhythm cardiac cycle overlaid on the physical map.

In some embodiments, the probe includes an intracardiac catheter having multiple electrodes that simultaneously generate respective sets of the signals.

In additional embodiments, the non-sinus rhythm cardiac cycle includes a premature ventricular contraction.

In further embodiments, generating the physical map includes generating the physical map based on the 3D locations indicated by the sets of signals received during the first and second cardiac cycles. In one embodiment, generating the physical map includes generating a first physical map based on the 3D locations indicated by the sets of signals received during the first cardiac cycle and a second physical map based on the 3D locations indicated by the sets of signals received during the second cardiac cycle, and selecting either the first or the second physical map. In another embodiment, the second physical map is in accordance with the first physical map.

In supplemental embodiments, rendering the electroanatomic map including the local activation times for the non-sinus rhythm cardiac cycle overlaid on the physical map includes overlaying the local activation time of the non-sinus rhythm cardiac cycle indicated by each given signal at a map location corresponding to the 3D location indicated by the given signal.

In some embodiments, comparing the received electrical potential measurements and the respective times to a given template includes comparing a given signal indicating the received electrical potential measurements and the respective times to the given template.

In additional embodiments, the method may include identifying a region of the map having earliest local activation times, and flagging, on the display, the identified region for ablation. In one embodiment, identifying the region of the map having earliest local activation times includes segmenting the map into multiple regions based on their respective local activation times, and identifying the region having the earliest local activation times.

There is also provided, in accordance with an embodiment of the present invention, an apparatus including a display, and a processor configured to receive sets of signals during multiple cardiac cycles, each set of the signals indicating, for a medical probe inserted into a cardiac chamber, a three-dimensional (3D) location of a distal end of the probe, electrical potentials measured at the 3D location, and respective times during a given cardiac cycle when the electrical potentials were measured, to compare the received electrical potential measurements and the respective times to a first template for a sinus rhythm cardiac cycle and a second template for a non-sinus rhythm cardiac cycle so as to identify a sequence of cardiac cycles including consecutive first, second, and third cardiac cycles wherein the first and second cardiac cycles are in accordance with the first template and the third cardiac cycle is in accordance with the second template, to generate a physical map of the cardiac chamber, based on the 3D locations, and to render to a display, based on the received 3D locations and corresponding measured electrical potentials, an electroanatomic map including the local activation times for the non-sinus rhythm cardiac cycle overlaid on the physical map.

There is further provided, in accordance with an embodiment of the present invention, a computer software product, operated in conjunction with a medical probe for insertion into a body cavity, the product including a non-transitory computer-readable medium, in which program instructions are stored, which instructions, when read by a computer, cause the computer to receive sets of signals during multiple cardiac cycles, each set of the signals indicating, for a medical probe inserted into a cardiac chamber, a three-dimensional (3D) location of a distal end of the probe, electrical potentials measured at the 3D location, and respective times during a given cardiac cycle when the electrical potentials were measured, to compare the received electrical potential measurements and the respective times to a first template for a sinus rhythm cardiac cycle and a second template for a non-sinus rhythm cardiac cycle so as to identify a sequence of cardiac cycles including consecutive first, second, and third cardiac cycles wherein the first and second cardiac cycles are in accordance with the first template and the third cardiac cycle is in accordance with the second template, to generate a physical map of the cardiac chamber, based on the 3D locations, and to render to a display, based on the received 3D locations and corresponding measured electrical potentials, an electroanatomic map including the activation times for the non-sinus rhythm cardiac cycle overlaid on the physical map.

BRIEF DESCRIPTION OF THE DRAWINGS

The disclosure is herein described, by way of example only, with reference to the accompanying drawings, wherein.

DETAILED DESCRIPTION OF EMBODIMENTS

Generating a local activation time (LAT) map of a heart with an arrhythmia is typically a difficult and time-consuming process. The LAT map is generated from information collected during sinus and non-sinus cardiac cycles, and the selection of the different types of cardiac cycles (also known as beats) by a medical professional (e.g., a physician) can be time consuming.

Embodiments of the present invention provide methods and systems for automatically generating an electroanatomic LAT hybrid map that maps premature ventricular contractions (PVCs) for an arrhythmic heart. As described hereinbelow, an intra-cardiac probe is inserted into a cardiac chamber, and sets of signals are received during multiple cardiac cycles, each set of the signals indicating a three-dimensional (3D) location of a distal end of the probe, electrical potentials measured at the 3D location, and respective times during a given cardiac cycle when the electrical potentials were measured.

The received electrical potential measurements and the respective times are compared to a first template for a normal sinus rhythm (also referred to herein simply as sinus rhythm) cardiac cycle and a second template for a non-sinus rhythm cardiac cycle so as to identify a sequence of cardiac cycles comprising consecutive first, second, and third cardiac cycles, wherein the first and second cardiac cycles are in accordance with the first template and the third cardiac cycle is in accordance with the second template. A physical map of the cardiac chamber is generated based on the received 3D locations, and based on the received 3D locations and corresponding measured electrical potentials, an electroanatomic map comprising the local activation times for the non-sinus rhythm cardiac cycle overlaid on the physical map is rendered to a display. The resultant map may then typically be used to select a region for ablation, since it indicates an origin of the PVC. Using templates to identify sinus and non-sinus cardiac cycles enables systems implementing embodiments of the present invention to rapidly generate electroanatomic LAT maps for an arrhythmic heart without requiring any user input to identify the sinus and non-sinus cardiac cycles. In some embodiments, the physical map may be generated solely based on the 3D coordinates received during the first and second cardiac cycles (i.e., the sinus rhythm cardiac cycles). By only using 3D location coordinates collected from the sinus rhythm cardiac cycles, embodiments of the present invention can produce a more stable physical map having fewer errors due to the unstable or "jumpy" nature of adjacent non-sinus cardiac cycles such as PVCs.

System Description

Figure 1A:
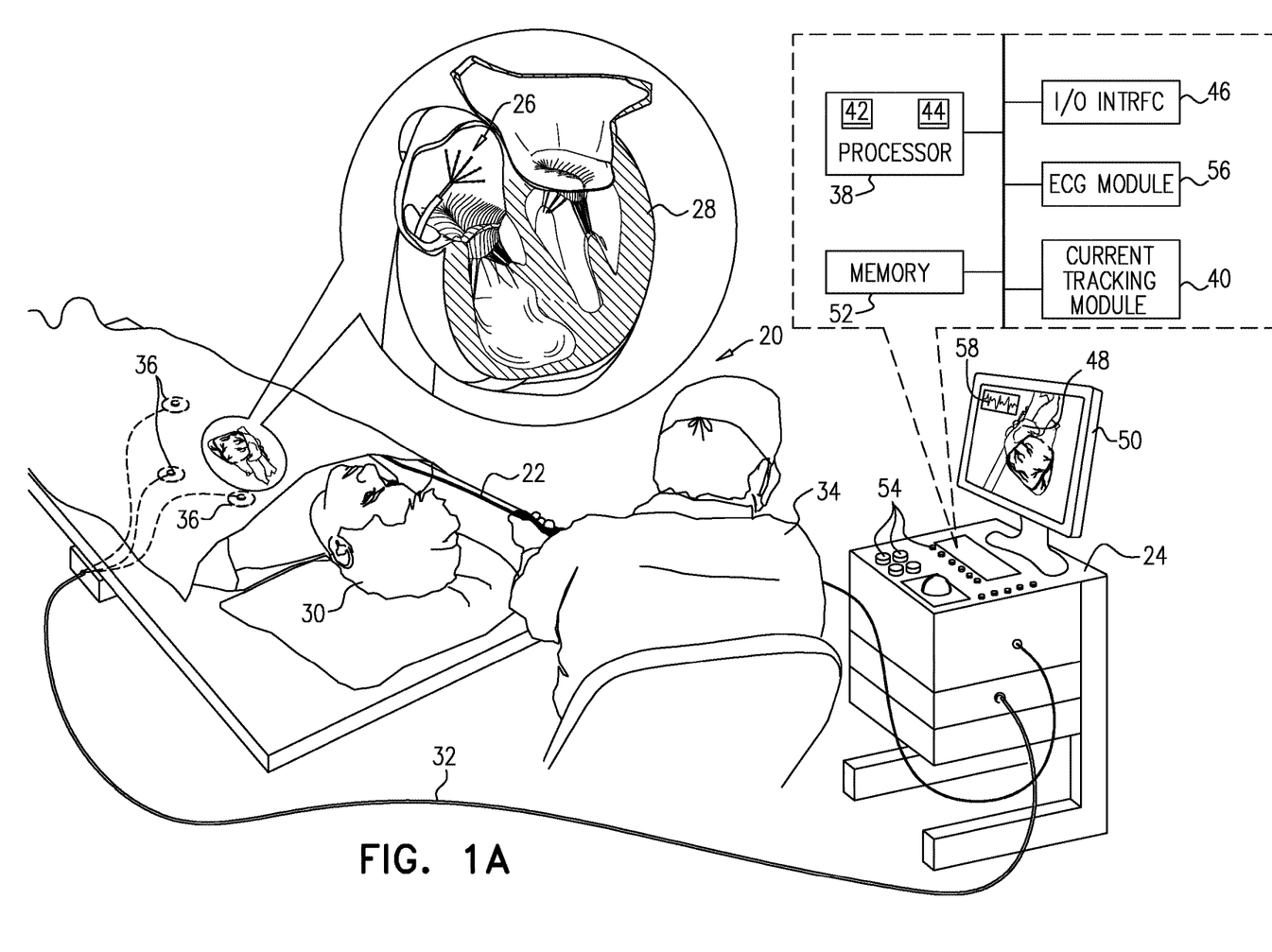
FIGS. 1A and 1B, are schematic, pictorial illustrations of a medical system comprising a mapping catheter, in accordance with an embodiment of the present invention.
Figure 1B:
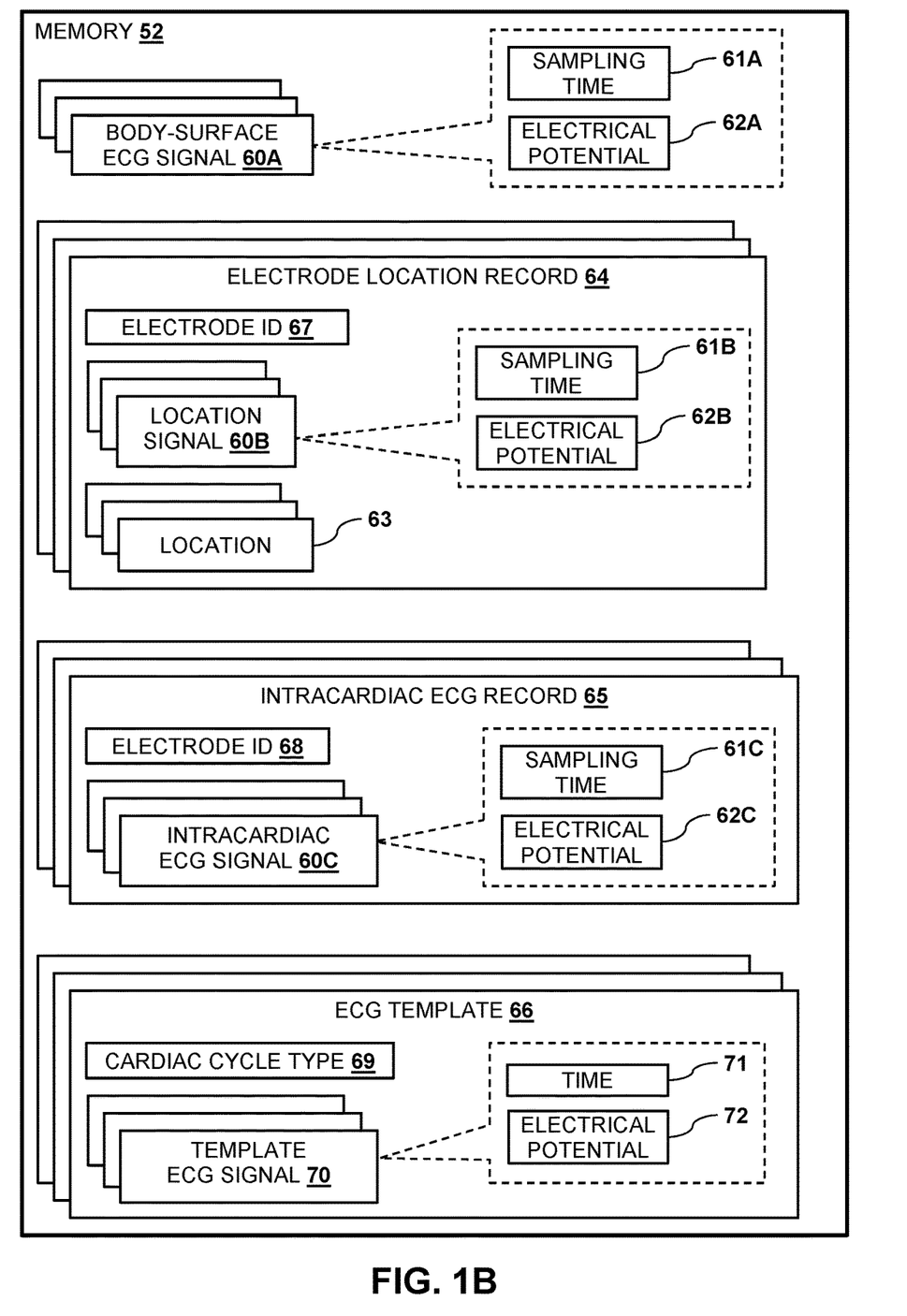
Figure 2:
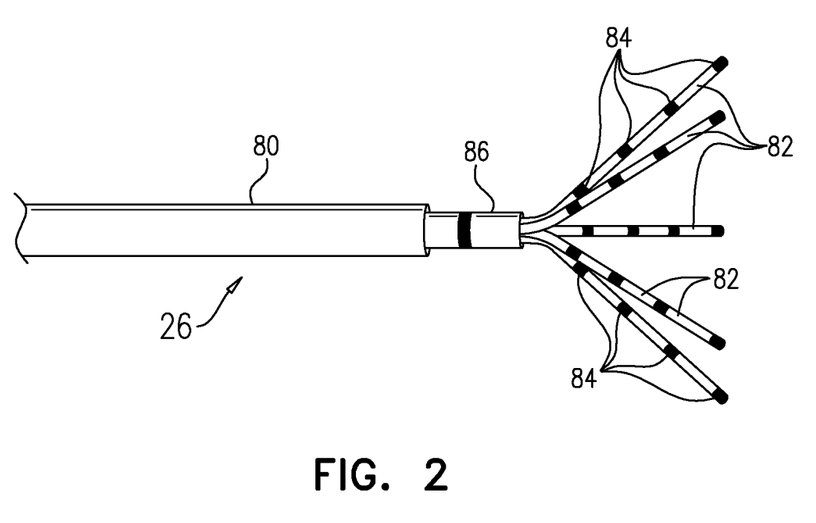
FIG. 2 is a schematic pictorial illustration of a distal end of the mapping catheter, in accordance with an embodiment of the present invention.

FIGS. 1A and 1B are schematic, pictorial illustrations of a medical system 20 comprising a medical probe 22 and a control console 24, and FIG. 2 is a schematic pictorial illustration of a distal end 26 of the medical probe 22, in accordance with an embodiment of the present invention. Medical system 20 may be based, for example, on the CARTO® system, produced by Biosense Webster Inc. of 33 Technology Drive, Irvine, Calif. 92618 USA. In embodiments described hereinbelow, medical probe 22 can be used for diagnostic or therapeutic treatment, such as for such as mapping electrical potentials of a heart 28 of a patient 30. In embodiments described herein, medical probe may also be referred to as a mapping catheter. Alternatively, medical probe 22 may be used, mutatis mutandis, for other therapeutic and/or diagnostic purposes in the heart or in other body organs.

During a medical procedure, a medical professional 34 inserts medical probe 22 into a biocompatible sheath 80 (FIG. 2) that has been pre-positioned in a body cavity (e.g., a chamber of heart 28) of the patient so that distal end 26 of the medical probe enters the body cavity. By way of example, as shown in FIG. 2, distal end 26 of probe 22 comprises flexible splines 82 that are formed at the end of a tubular shaft 86. During a medical procedure, medical professional 34 can deploy splines 82 by extending tubular shaft from sheath 80.

Control console 24 is connected, by a cable 32, to body surface electrodes, which typically comprise adhesive skin patches 36 that are affixed to patient 30. Control console 24 comprises a processor 38 that, in conjunction with a current tracking module 40, determines position coordinates of the distal end 26 inside the heart based on impedances measured between adhesive skin patches 36 and electrodes 84 that are affixed to splines 82 as shown in FIG. 2. In embodiments described herein, electrodes 84 can also be configured to apply a signal to tissue in heart 28, and/or to measure a certain physiological property (e.g., the local surface electrical potential) at a location in the heart. Electrodes 84 are connected to control console 24 by wires (not shown) running through medical probe 22.

While embodiments herein show probe 20 comprising a multi-spline intracardiac catheter such as the Pentaray® NAV catheter, using other multi-electrode intracardiac catheters such as the Navistar® Thermocool® catheters are considered to be within the spirit and scope of the present invention. The Pentaray® NAV and Navistar® Thermocool® catheters are both produced by Biosense Webster Inc.

Processor 38 may comprise real-time noise reduction circuitry 42 typically configured as a field programmable gate array (FPGA), followed by an analog-to-digital (A/D) ECG (electrocardiograph) signal conversion integrated circuit 44. The processor can pass the signal from A/D ECG circuit 42 to another processor and/or can be programmed to perform one or more algorithms disclosed herein, each of the one or more algorithms comprising steps described hereinbelow. The processor uses circuitry 42 and circuit 44, as well as features of modules which are described in more detail below, in order to perform the one or more algorithms.

The medical system shown in FIGS. 1A, 1B, and 2 uses impedance-based sensing to measure a location of distal end 26, but other position tracking techniques may be used (e.g., techniques using magnetic-based sensors). Impedance-based position tracking techniques are described, for example, in U.S. Pat. Nos. 5,983,126, 6,456,864 and 5,944,022, whose disclosures are incorporated herein by reference. Magnetic position tracking techniques are described, for example, in U.S. Pat. Nos. 5,391,199, 5,443,489, 6,788,967, 6,690,963, 5,558,091, 6,172,499 and 6,177,792, whose disclosures are incorporated herein by reference. The methods of position sensing described hereinabove are implemented in the above-mentioned CARTO® system and are described in detail in the patents cited above.

Control console 24 also comprises an input/output (I/O) communications interface 46 that enables the control console to transfer signals from, and/or transfer signals to electrodes 84 and adhesive skin patches 36. Based on signals received from electrodes 84 and/or adhesive skin patches 36, processor 38 can generate an electroanatomic local activation time (LAT) map 48 that presents measurements of cardiac conduction velocity, as described in the description referencing FIG. 5 hereinbelow.

During a procedure, processor 38 can present electroanatomic LAT map 48 to medical professional 34 on a display 50, and store data representing the electroanatomic LAT map in a memory 52. Memory 52 may comprise any suitable volatile and/or non-volatile memory, such as random access memory or a hard disk drive. In some embodiments, medical professional 34 can manipulate map 48 using one or more input devices 54. In alternative embodiments, display 50 may comprise a touchscreen that can be configured to accept inputs from medical professional 34, in addition to presenting map 48.

As shown in FIG. 1B, memory 52 stores signals 60 received by processor 38, each given signal 60 comprising an ordered pair of a sampling time 61 indicating when the given signal was received, and an electrical potential 62 measured by adhesive skin patches 36 or a given electrode 84, as described hereinbelow. In FIG. 1B, signals 60 and their respective sampling times 61 and electrical potentials are differentiated by appending a letter to the identifying numeral, so that the signals comprise signals 60A-60C, the sampling times comprise sampling times 61A-61C, and the electrical potentials comprise electrical potentials 62A-62C. In embodiments described herein, signals 60A comprise body-surface ECG signals received from patches 36, signals 60B comprise location signals received from patches 36 and indicating respective locations 63 of electrodes 84, and signals 60C comprise intracardiac ECG signals received from electrodes 84.

In the configuration shown in FIG. 1B, memory 52 also stores a set of electrode location records 64, a set of intracardiac ECG records 65, and a set of ECG templates 66. Each electrode location record 64 comprises an electrode identifier (ID) 67 indicating a given electrode 84, a set of location signals 60B received from adhesive skin patches 36 for the given electrode, and a set of locations 63 having a one-to-one correspondence with electrodes 84. Each given location 63 typically comprises a set of 3D coordinates generated from its corresponding electrical potentials 62B.

In some embodiments, electrode location records 64 have a one-to-one correspondence with electrodes 84, and processor 38 can initialize the set of electrode location records 64 by storing, to each electrode ID 67, a unique numeric value or text string indicating the corresponding electrode 84.

Each intracardiac ECG record 65 comprises an electrode ID 68 indicating a given electrode 84, and a set of intracardiac ECG signals 60C received from the indicated electrode. In some embodiments, intracardiac ECG records 65 have a one-to-one correspondence with electrodes 84, and processor 38 can initialize the set of intracardiac ECG records 65 by storing, to each electrode ID 68, a unique numeric value or text string indicating the corresponding electrode 84.

Each ECG template 66 comprises a cardiac cycle type 69 and a corresponding set of template ECG signals 70, each of the template ECG signals comprising a time 71 and an electrical potential 72. Examples of cardiac cycle types 69 include, but are not limited to, a normal sinus rhythm, and a non-sinus rhythm such as a premature ventricular contraction (PVC).

In operation, processor 38 can receive signals 60, and store the received signals to memory 52 using the following embodiments:

Processor 38 receives a set of body-surface ECG signals 60A from adhesive skin patches 36, and stores the received set of body-surface ECG signals to memory 52.

Processor 38 receives, from adhesive skin patches 36, respective sets of location signals 60B for each electrode 84. Upon receiving a given set of location signals 60B for a given electrode 84, processor 38 can use embodiments described supra to compute locations 63 corresponding to electrical potentials 62B in the given set of location signals 60B. Processor 38 can then identify a given electrode location record 64 whose electrode ID 67 indicates the given electrode, and store the given set of location signals 60B and corresponding locations 63 to the identified electrode location record.

Processor 38 receives, from electrodes 84, respective sets of intracardiac ECG signals 60C. Upon receiving each given set of intracardiac signals 60C from a given electrode 84, processor 38 can identify a given intracardiac ECG record 65 whose electrode ID 69 indicates the given electrode, and store the given set of intracardiac ECG signals 60C to the identified intracardiac ECG record.

Control console 24 may also comprise an electrocardiogram (ECG) module 56 that can be configured to generate an ECG chart 58 from body surface ECG signals 60A. In some embodiments, processor 38 presents ECG chart 58 on display 50 (i.e., along with LAT map 48). In addition to presenting ECG chart 58 on display 50, processor 38 can store the ECG chart to memory 52. Further details of ECG chart 58 are described in the description referencing FIG. 5 hereinbelow.

Mapping

Figure 3:
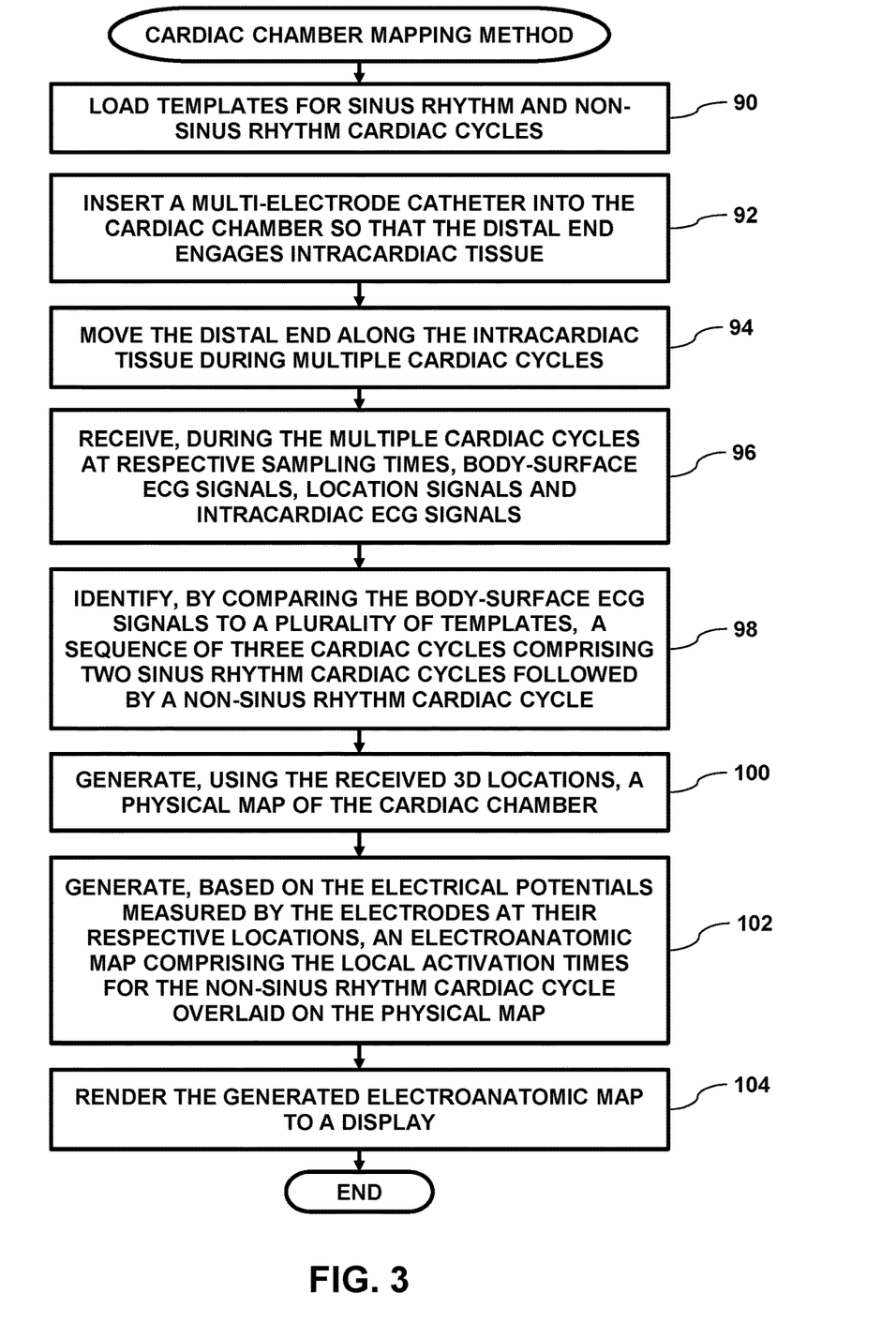
FIG. 3 is a flow diagram that schematically illustrates a method of using the mapping catheter for a mapping procedure that generates a map of a cardiac chamber based on signals collected during sinus and non-sinus cardiac cycles, in accordance with an embodiment of the present invention.
Figure 4:
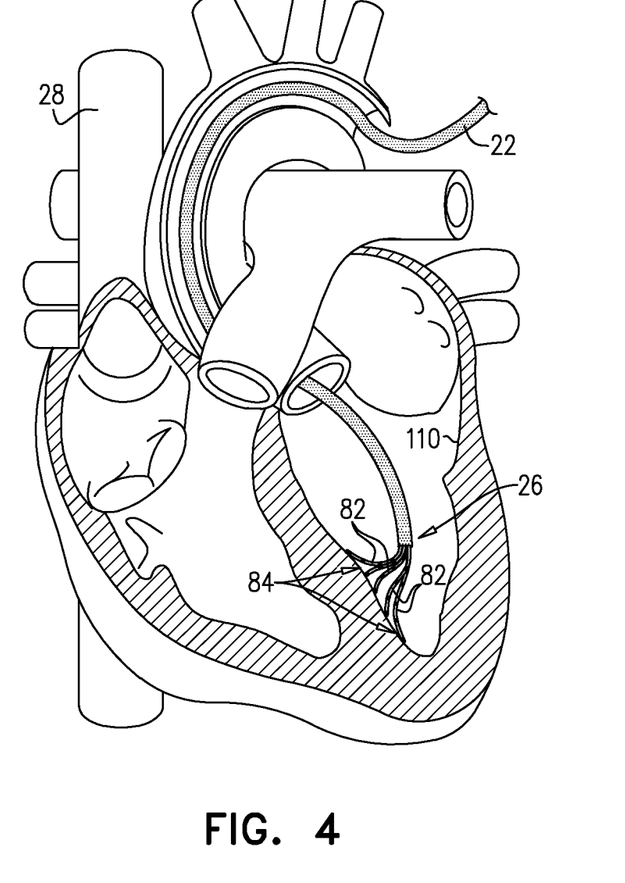
FIG. 4 is a schematic detail view of the distal end of the mapping catheter in the cardiac chamber during the mapping procedure, in accordance with an embodiment of the present invention.

FIG. 3 is a flow diagram that schematically illustrates a method for mapping a chamber of heart 28, and FIG. 4 is a schematic detail view of splines 82 engaging intracardiac tissue 110 in the chamber, in accordance with an embodiment of the present invention. In a load step 90, processor 38 loads, to memory 52, a plurality of templates 60 comprising at least one template 60 for a sinus rhythm cardiac cycles and at least one template 60 for a non-cardiac cardiac cycle.

In an insertion step 92, medical professional 34 inserts distal end 26 into the chamber so that splines 82 engage intracardiac tissue 110, and in a maneuvering step 94, medical professional 34 moves the splines at the distal end along intracardiac tissue 110 during multiple cardiac cycles. As medical professional 34 moves the splines along the intracardiac tissue during the multiple cardiac cycles, processor 38 receives, in a receiving step 96, body-surface ECG signals 60A, location signals 60B and intracardiac ECG signals 60C.

In identification step 98, processor 38 identifies, by comparing the received body-surface ECG signals 60A to ECG templates 66, three consecutive cardiac cycles comprising two sinus cardiac rhythm cycles followed by a non-sinus rhythm cardiac cycle. In some embodiments, comparing body-surface ECG signals 60A to templates 66 comprises comparing sampling times 61A and the electrical potentials 62A in the body-surface ECG signals to times 71 and electrical potentials 72 in the templates.

As described supra, a first given template 66 can be defined for a sinus rhythm cardiac cycle, and a second given template 66 can be defined for a non-sinus rhythm cardiac cycle such as a premature ventricular contraction. In embodiments of the present invention, processor 38 can identify the three cardiac cycles by comparing body-surface ECG signals 60A to templates 66 and detecting that the body-surface ECG signals during the first two cardiac cycles match a first given template 66 for a sinus rhythm cardiac cycle, and detecting that the body-surface ECG signals during the subsequent third cardiac cycle match a second given template 66 for a non-sinus rhythm cardiac cycle. Therefore, processor 38 can identify a first set sampling times 61 for the first two cardiac cycles and a second set of sampling times 61 for the third cardiac cycle.

To match, during a given cardiac cycle, body-surface ECG signals 60A to a given template 66, processor 38 can perform a correlation between the body-surface ECG signals and the given template, and detect a match by comparing the correlation to predefined thresholds, and determining there is a high correlation (i.e., within a defined threshold) between the body-surface ECG signals and the given template. For example, processor 38 can use a correlation threshold of 0.95 when comparing body-surface ECG signals 60A to a given template 66 for a non-sinus rhythm cardiac cycle, and can use a correlation threshold of 0.9 when comparing the body-surface ECG signals to a given template 62 for a sinus rhythm cardiac cycle.

Figure 5:
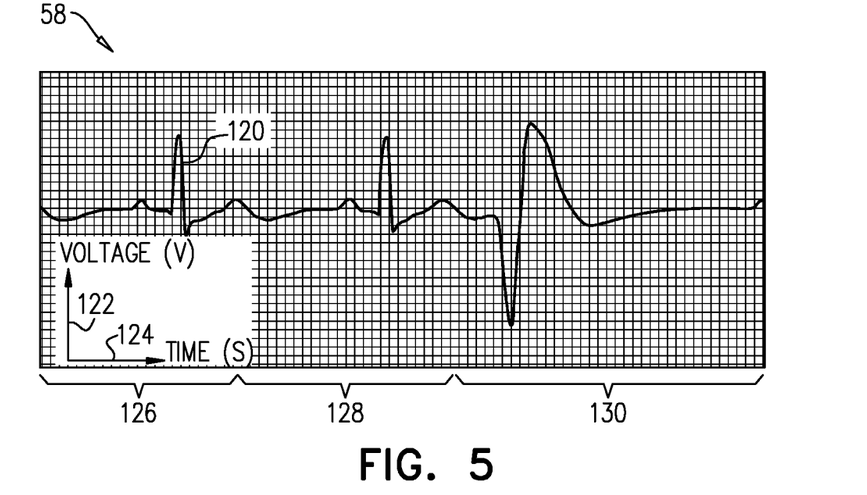
FIG. 5 is a schematic view of an electrocardiogram during the sinus and non-sinus cardiac cycles, in accordance with an embodiment of the present invention.

FIG. 5 is a schematic pictorial illustration of ECG chart 58, in accordance with an embodiment of the present invention. ECG chart 58 comprises a trace comprising a line 120 that plots electrical potentials 61A in a given set of body-surface ECG signal 60A along a vertical axis 122 against time along a horizontal axis 124, wherein electrical potentials 61A are measured as voltages V and the time is measured in seconds S. In the example shown in FIG. 5, line 120 shows electrical potentials 61A in a given set of body-surface ECG signals 60A measured during a sequence of consecutive cardiac cycles 126, 128 and 130, wherein cardiac cycles 126 and 128 are sinus rhythm, and wherein cardiac cycle 130 comprises a premature ventricular contraction (i.e., an example of a non-sinus rhythm cardiac cycle).

Returning to the flow chart, in a first generation step 100, processor 38 generates, based on 3D coordinates indicated by locations 63, a physical map of the cardiac chamber. The physical map is described in the description referencing FIG. 6, hereinbelow. In some embodiments, processor 38 uses 3D coordinates indicated by locations 63 from location signals 60B whose respective sampling times 61B were during the two sinus rhythm cardiac cycles in order to create a more stable physical map (i.e., ignoring 3D coordinates indicated by locations 63 from location signals 60B whose respective sampling times 61B were during the non-sinus rhythm cardiac cycle), as described supra.

Using a physical map comprising 3D coordinates indicated by locations 63 from location signals 60B whose respective sampling times 61B were during normal sinus-rhythm cardiac cycles can help create a more useful physical map since heart 28 is typically in sinus rhythm most of the time. For example, during an ablation procedure using an ablation catheter (not shown), if the non-sinus cardiac cycles comprise PVCs, heart 28 will typically be in sinus rhythm, with intermittent short PVC bursts. Therefore if processor 38 creates the physical map with 3D coordinates indicated by locations 63 from location signals 60B whose respective sampling times 61B were during a PVC cardiac cycle, a discrepancy likely exists between the locations of the map's points (PVC geometry) and distal end 26, as the ablation catheter location is displayed mostly in sinus rhythm. As a result, any ablated area may not be optimum to correct the patient's arrhythmia. It is believed that the geometry of the heart differs during sinus rhythm, compared to its geometry during non-sinus cardiac cycles such as PVCs.

In additional embodiments, processor 38 can generate the physical map by creating a first physical map for the 3D coordinates indicated by locations 63 from location signals 60B whose respective sampling times 61B were during the first (i.e., sinus rhythm) cardiac cycle, creating a second physical map for the 3D coordinates indicated by locations 63 from location signals 60B whose respective sampling times 61B were during the second (i.e., sinus rhythm) cardiac cycle, and selecting either the first of the second physical map as physical map. The physical map is described in the description referencing FIG. 6 hereinbelow.

In some embodiments, processor 38 can generate the physical map only if body-surface ECG signals 60A whose respective sampling times 61A were during the first and second sinus rhythm cardiac cycles match (i.e., within a specified threshold) a given template 66 for a sinus rhythm cardiac cycle. In other words, processor 38 can generate the physical map only if the first and the second maps are substantially the same (i.e., in accordance with one another).

In a second generation step 102, processor 38 generates, based on locations 63 (i.e., as indicated in the location signals) and the corresponding electrical potentials 62C measured by electrodes 84 (i.e., as indicated in the intracardiac ECG signals), map 48 comprising local activation times for the non-sinus rhythm cardiac cycle overlaid on the physical map. (U.S. Patent Application 2015/0073246, whose disclosure is incorporated herein by reference, describes overlaying PVC electrical data on a sinus rhythm physical map.) In other words, map 48 reflects the geometry of heart 28 during sinus rhythm, but has the local activation times of the heart while experiencing PVCs.

Finally, in a rendering step 104, processor 38 renders map 48 to display 50, and the method ends. To render map 48, processor 38 can render physical map 140 on display 50, and overlay, on the physical map rendered on the display, the local activation time of the non-sinus rhythm cardiac cycle indicated by each given intracardiac ECG signal 60C at a map location corresponding to the location indicated by the corresponding location signal (i.e., where sampling times 61B and 61C match). An example of overlaying the local activation times on the physical map is described in the description referencing FIG. 6 hereinbelow.

Figure 6:
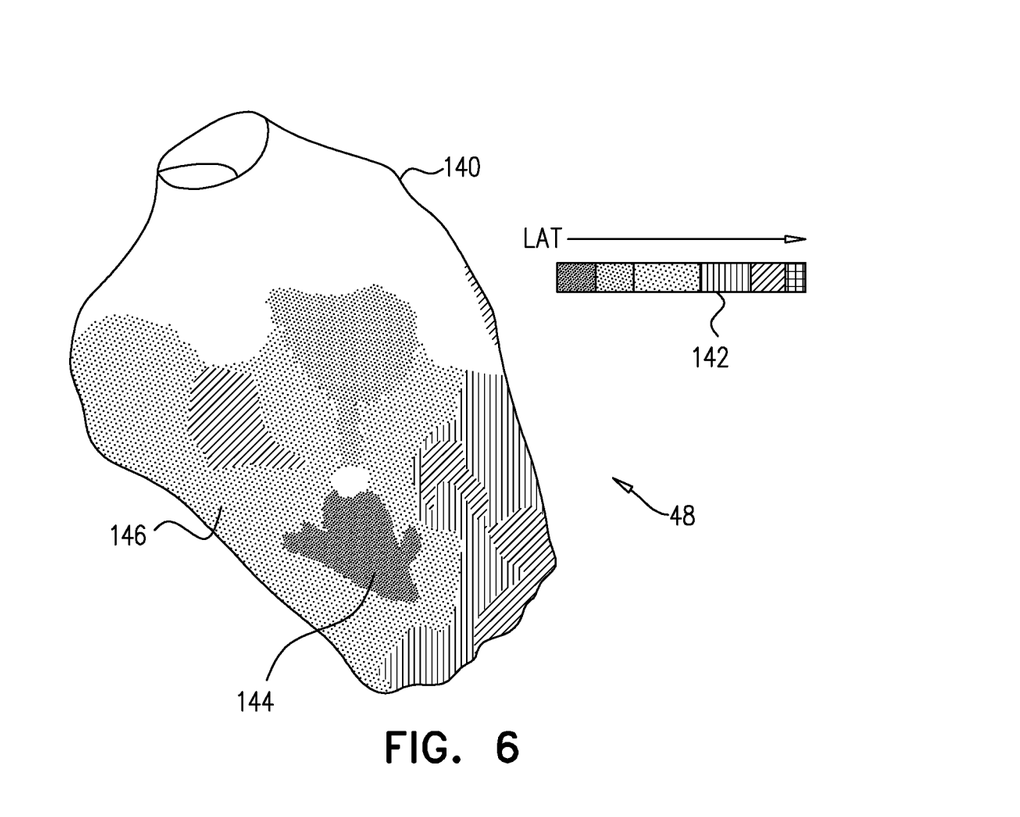
FIG. 6 is a schematic view of an electroanatomic map comprising first local activation times for the sinus rhythm cardiac cycles and a second local activation time for the non-sinus rhythm cardiac cycle overlaid on a physical map of the cardiac chamber, in accordance with an embodiment of the present invention.

FIG. 6 is a schematic pictorial illustration showing a section of LAT map 48 that comprises a physical map 140 of a chamber of heart 28, in accordance with an embodiment of the present invention. In FIG. 6, local activation time information for map 48 is incorporated into physical map 140 and coded using patterns in accordance with a key 142. These patterns simulate the pseudocolors of an actual functional map. The patterns in key 142 correspond, from left to right, to a range of early to late LAT times (i.e., with regard to a reference time for a given cardiac cycle).

Therefore, in map 48, a first region 144 has a relatively early LAT, and is circumscribed by an area 146 that has a relatively later local activation time. In embodiments described herein, regions 144 and 146 comprise map locations that correspond to the 3D locations indicated by the received signals. In operation, since region 144 processor 38 can identify and flag region 144 (i.e., the region with the earliest LAT in map 48) as the region for ablation. Alternatively, medical professional can use input devices 54 to select and flag regions 144 and/or 146.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method of mapping local activation times for sinus and non-sinus cardiac cycles, the method comprising:

receiving, by a processor, sets of signals during multiple cardiac cycles, each set of the signals indicating, for a medical probe inserted into a cardiac chamber, a three-dimensional (3D) location of a distal end of the probe, electrical potentials measured at the 3D location, and respective times during a given cardiac cycle when the electrical potentials were measured;

comparing the received electrical potential measurements and the respective times to a first template for a sinus rhythm cardiac cycle and a second template for a non-sinus rhythm cardiac cycle so as to identify a sequence of cardiac cycles comprising consecutive first, second, and third cardiac cycles wherein the first and second cardiac cycles are in accordance with the first template and the third cardiac cycle is in accordance with the second template;

generating a physical map of the cardiac chamber, based on the 3D locations; and rendering to a display, based on the received 3D locations and corresponding measured electrical potentials, an electroanatomic map comprising the local activation times for the non-sinus rhythm cardiac cycle overlaid on the physical map.

2. The method according to claim 1, wherein the probe comprises an intracardiac catheter having multiple electrodes that simultaneously generate respective sets of the signals.

3. The method according to claim 1, wherein the non-sinus rhythm cardiac cycle comprises a premature ventricular contraction.

4. The method according to claim 1, wherein generating the physical map comprises generating the physical map based on the 3D locations indicated by the sets of signals received during the first and second cardiac cycles.

5. The method according to claim 4, wherein generating the physical map comprises generating a first physical map based on the 3D locations indicated by the sets of signals received during the first cardiac cycle and a second physical map based on the 3D locations indicated by the sets of signals received during the second cardiac cycle, and selecting either the first or the second physical map.

6. The method according to claim 5, wherein the second physical map is in accordance with the first physical map.

7. The method according to claim 1, wherein rendering the electroanatomic map comprising the local activation times for the non-sinus rhythm cardiac cycle overlaid on the physical map comprises overlaying the local activation time of the non-sinus rhythm cardiac cycle indicated by each given signal at a map location corresponding to the 3D location indicated by the given signal.

8. The method according to claim 1, wherein comparing the received electrical potential measurements and the respective times to a given template comprises comparing a given signal indicating the received electrical potential measurements and the respective times to the given template.

9. The method according to claim 1, and comprising identifying a region of the map having earliest local activation times, and flagging, on the display, the identified region for ablation.

10. The method according to claim 9, wherein identifying the region of the map having earliest local activation times comprises segmenting the map into multiple regions based on their respective local activation times, and identifying the region having the earliest local activation times.

11. An apparatus for mapping local activation times for sinus and non-sinus cardiac cycles, the apparatus comprising:
a display; and
a processor configured:
to receive sets of signals during multiple cardiac cycles, each set of the signals indicating, for a medical probe inserted into a cardiac chamber, a three-dimensional (3D) location of a distal end of the probe, electrical potentials measured at the 3D location, and respective times during a given cardiac cycle when the electrical potentials were measured,
to compare the received electrical potential measurements and the respective times to a first template for a sinus rhythm cardiac cycle and a second template for a non-sinus rhythm cardiac cycle so as to identify a sequence of cardiac cycles comprising consecutive first, second, and third cardiac cycles
wherein the first and second cardiac cycles are in accordance with the first template and the third cardiac cycle is in accordance with the second template,
to generate a physical map of the cardiac chamber, based on the 3D locations, and
to render to the display, based on the received 3D locations and corresponding measured electrical potentials, an electroanatomic map comprising the local activation times for the non-sinus rhythm cardiac cycle overlaid on the physical map.

12. The apparatus according to claim 11, wherein the probe comprises an intracardiac catheter having multiple electrodes that simultaneously generate respective sets of the signals.

13. The apparatus according to claim 11, wherein the non-sinus rhythm cardiac cycle comprises a premature ventricular contraction.

14. The apparatus according to claim 11, wherein the processor is configured to generate the physical map by generating the physical map based on the 3D locations indicated by the sets of signals received during the first and second cardiac cycles.

15. The apparatus according to claim 14, wherein the processor is configured to generate the physical map by generating a first physical map based on the 3D locations indicated by the sets of signals received during the first cardiac cycle and a second physical map based on the 3D locations indicated by the sets of signals received during the second cardiac cycle, and selecting either the first or the second physical map.

16. The apparatus according to claim 15, wherein the second physical map is in accordance with the first physical map.

17. The apparatus according to claim 11, wherein the processor is configured to render the electroanatomic map comprising the local activation times for the non-sinus rhythm cardiac cycle overlaid on the physical map by overlaying the local activation time of the non-sinus rhythm cardiac cycle indicated by each given signal at a map location corresponding to the 3D location indicated by the given signal.

18. The apparatus according to claim 11, wherein the processor is configured to compare the received electrical potential measurements and the respective times to a given template comprises comparing a given signal indicating the received electrical potential measurements and the respective times to the given template.

19. The apparatus according to claim 11, wherein the processor is further configured to identify a region of the map having earliest local activation times, and to flag, on the display, the identified region for ablation.

20. The apparatus according to claim 19, wherein the processor is configured to identify the region of the map having earliest local activation times by segmenting the map into multiple regions based on their respective local activation times, and identifying the region having the earliest local activation times.

21. A computer software product, operated in conjunction with a medical probe for insertion into a body cavity, the product comprising a non-transitory computer-readable medium, in which program instructions are stored, which instructions, when read by a computer, cause the computer:
to receive sets of signals during multiple cardiac cycles, each set of the signals indicating, for a medical probe inserted into a cardiac chamber, a three-dimensional (3D) location of a distal end of the probe, electrical potentials measured at the 3D location, and respective times during a given cardiac cycle when the electrical potentials were measured;
to compare the received electrical potential measurements and the respective times to a first template for a sinus rhythm cardiac cycle and a second template for a non-sinus rhythm cardiac cycle so as to identify a sequence of cardiac cycles comprising consecutive first, second, and third cardiac cycles wherein the first and second cardiac cycles are in accordance with the first template and the third cardiac cycle is in accordance with the second template;
to generate a physical map of the cardiac chamber, based on the 3D locations; and
to render to a display, based on the received 3D locations and corresponding measured electrical potentials, an electroanatomic map comprising the activation times for the non-sinus rhythm cardiac cycle overlaid on the physical map.

* * * * *